(12) United States Patent
Li et al.

(10) Patent No.: US 10,564,125 B2
(45) Date of Patent: Feb. 18, 2020

(54) SELF-ALIGNED NANOTIPS WITH TAPERED VERTICAL SIDEWALLS

(71) Applicant: International Business Machines Corporation, Armonk, NY (US)

(72) Inventors: Juntao Li, Cohoes, NY (US); Kangguo Cheng, Schenectady, NY (US); Peng Xu, Santa Clara, CA (US); Heng Wu, Guilderland, NY (US)

(73) Assignee: International Business Machines Corporation, Armonk, NY (US)

( * ) Notice: Subject to any disclaimer, the term of this patent is extended or adjusted under 35 U.S.C. 154(b) by 236 days.

(21) Appl. No.: 15/841,907

(22) Filed: Dec. 14, 2017

(65) Prior Publication Data

US 2019/0187097 A1    Jun. 20, 2019

(51) Int. Cl.
*G01N 27/68* (2006.01)
*B82B 3/00* (2006.01)
*B82B 1/00* (2006.01)

(52) U.S. Cl.
CPC ............. *G01N 27/68* (2013.01); *B82B 1/001* (2013.01); *B82B 3/0019* (2013.01)

(58) Field of Classification Search
CPC ...... G01N 27/68; B82B 1/001; B82B 3/0019; B81C 1/00031; B81B 2203/0361
See application file for complete search history.

(56) References Cited

U.S. PATENT DOCUMENTS

| | | | |
|---|---|---|---|
| 6,057,172 A | 5/2000 | Tomihari | |
| 6,607,415 B2 | 8/2003 | Dunfield et al. | |
| 6,960,528 B2 | 11/2005 | Chen et al. | |
| 7,799,707 B2 | 9/2010 | Baird et al. | |
| 7,932,548 B2 | 4/2011 | Nagashima | |
| 8,367,513 B2 | 2/2013 | Nagashima | |
| 8,395,199 B2 | 3/2013 | Nagashima | |
| 2005/0126913 A1* | 6/2005 | Burke | B03C 5/026 204/547 |
| 2007/0158661 A1 | 7/2007 | Lu et al. | |

(Continued)

FOREIGN PATENT DOCUMENTS

| | | |
|---|---|---|
| WO | 2006087588 A2 | 8/2006 |
| WO | 2014003901 A1 | 1/2014 |

OTHER PUBLICATIONS

Cui et al., Fabrication of high aspect ratio metal nanotips by nanosecond pulse laser melting, Nanotechnology, vol. 19, No. 34, 2008 (Year: 2008).*

(Continued)

*Primary Examiner* — Daniel R Miller
(74) *Attorney, Agent, or Firm* — Vazken Alexanian; Ryan, Mason & Lewis, LLP

(57) ABSTRACT

A method of forming a semiconductor structure includes forming a substrate, forming an anchor layer, and forming one or more self-aligned nanotip pillar pairs disposed vertically between the substrate and the anchor layer. A given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer. The bottom nanotip pillar and the top nanotip pillar comprise sidewalls that taper to points as distance from the respective base portions increases.

20 Claims, 12 Drawing Sheets

(56) References Cited

U.S. PATENT DOCUMENTS

| | | | | |
|---|---|---|---|---|
| 2011/0166045 A1* | 7/2011 | Dhawan | ............... | B82Y 10/00 |
| | | | | 506/39 |
| 2011/0193183 A1* | 8/2011 | Agarwal | ............. | B01J 19/0046 |
| | | | | 257/414 |
| 2013/0298977 A1 | 11/2013 | Chen et al. | | |
| 2019/0242846 A1* | 8/2019 | Taniguchi | ............. | B82Y 40/00 |

OTHER PUBLICATIONS

Esfandyarpour et al., Nanoelectronic three-dimensional (3D) nanotip sensing array for real-time, sensitive, label-free sequence specific detection of nucleic acids, Biomed Microdevices 18: 7, 2016 (Year: 2016).*

S.-W. Lee et al., "Fabrication of Nanometer-Scale Si Field Emitters Using Self-Assembled Ge Nanomasks," Journal of the Electrochemical Society, 2010, pp. H174-H177, vol. 157, No. 2.

C.-H. Hsu et al., "Generally Applicable Self-Masked Dry Etching Technique for Nanotip Array Fabrication," Nano Letters, Mar. 2004, pp. 471-475, vol. 4, No. 3.

X. Zhang et al., "Morphology and Wettability Control of Silicon Cone Arrays Using Colloidal Lithography," Langmuir, Jul. 7, 2009, pp. 7375-7382, vol. 25, No. 13.

F. Meng et al., "Dynamic Prebreakdown Current Measurement of Nanotips-Based Gas Ionization Sensor Application at Ambient Atmosphere," IEEE Sensors Journal, Apr. 2009, pp. 435-440, vol. 9, No. 4.

* cited by examiner

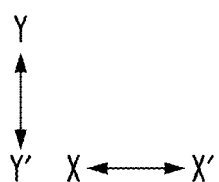
*FIG. 1*
100
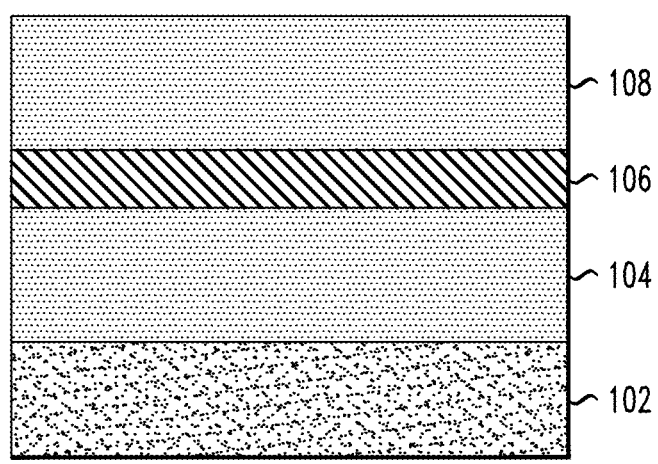

875

900

1000

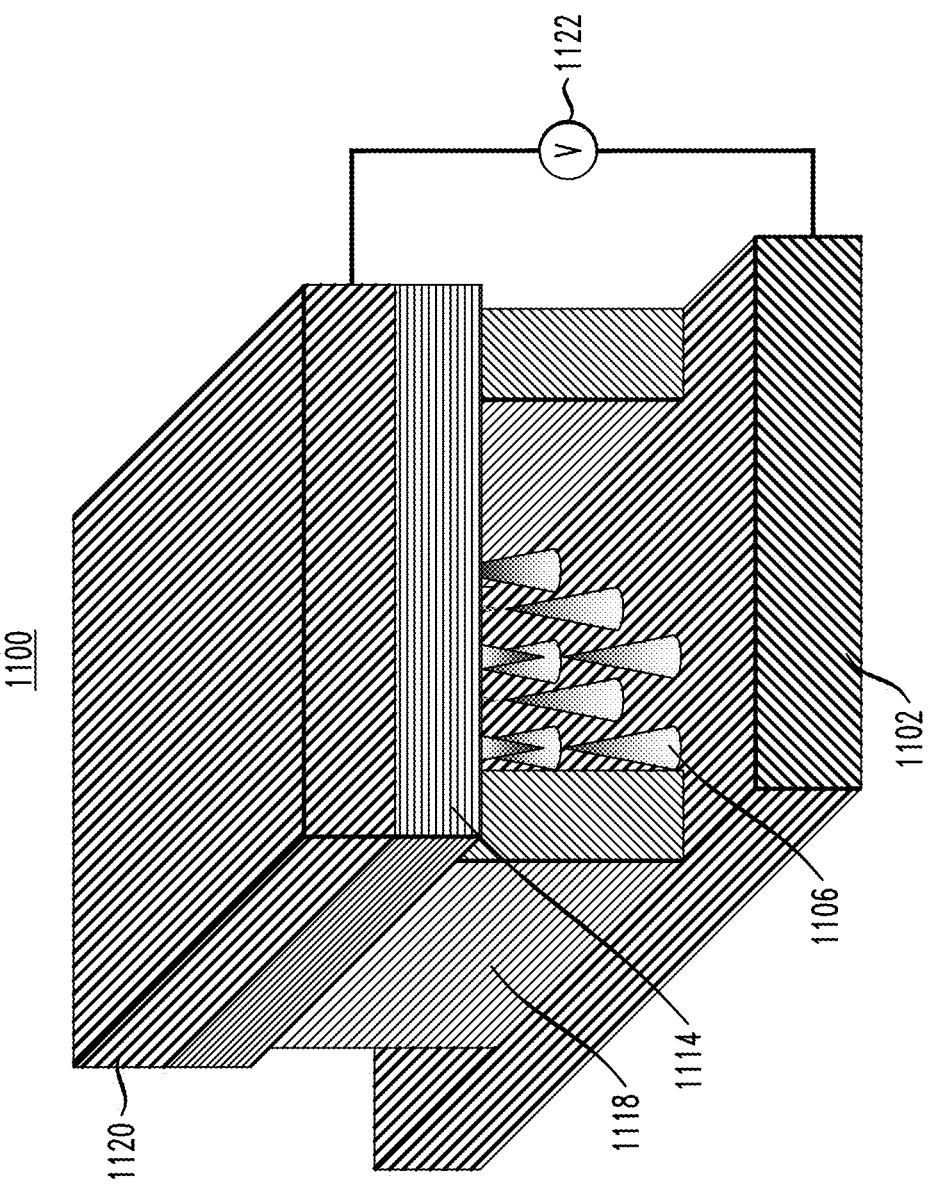

1200

1203

SELF-ALIGNED NANOTIPS WITH TAPERED VERTICAL SIDEWALLS

BACKGROUND

The present application relates to semiconductors, and more specifically, to techniques for forming semiconductor structures. Semiconductor structures may be formed with nanotips and other non-scale features. Recently, nanotips have attracted considerable interest because of distinctive differences in properties (e.g., electrical and optical properties) compared with bulk material. Nanotips are of increasing interest for numerous industries, due to potential for commercial application as, e.g., a field emission electron source, nanometer-cantilevers, nanoelectrodes, electro-chemical electrodes, nanoscale tips for scanning probe microscopy such as scanning tunneling and atom force microscopy, etc. Arrays of nanotips also have many potential applications, e.g., as field emitter arrays in vacuum microelectronic devices, as gas-ionization sensors, etc.

SUMMARY

Embodiments of the invention provide techniques for forming self-aligned nanometer-scale tips or nanotips, and other nanostructures.

In one embodiment, a method of forming a semiconductor structure comprises forming a substrate, forming an anchor layer, and forming one or more self-aligned nanotip pillar pairs disposed vertically between the substrate and the anchor layer. A given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer. The bottom nanotip pillar and the top nanotip pillar comprise sidewalls that taper to points as distance from the respective base portions increases.

In another embodiment, a semiconductor structure comprises a substrate, an anchor layer, and one or more self-aligned nanotip pillar pairs disposed vertically between the substrate and the anchor layer. A given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer. The bottom nanotip pillar and the top nanotip pillar comprise sidewalls that taper to points as distance from the respective base portions increases.

In another embodiment, an integrated circuit comprises a gas ionization sensor comprising a substrate, an anchor layer, and one or more self-aligned nanotip pillar pairs disposed vertically between the substrate and the anchor layer. A given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer. The bottom nanotip pillar and the top nanotip pillar comprise sidewalls that taper to points as distance from the respective base portions increases.

BRIEF DESCRIPTION OF THE DRAWINGS

FIG. 1 depicts a side cross-sectional view of a semiconductor structure comprising semiconductor layers formed over a substrate, according to an embodiment of the invention.

FIG. 11 depicts a perspective view of a sensor with an array of self-aligned cylindrical nanotip pillars, according to an embodiment of the invention.

DETAILED DESCRIPTION

Figure 2A:
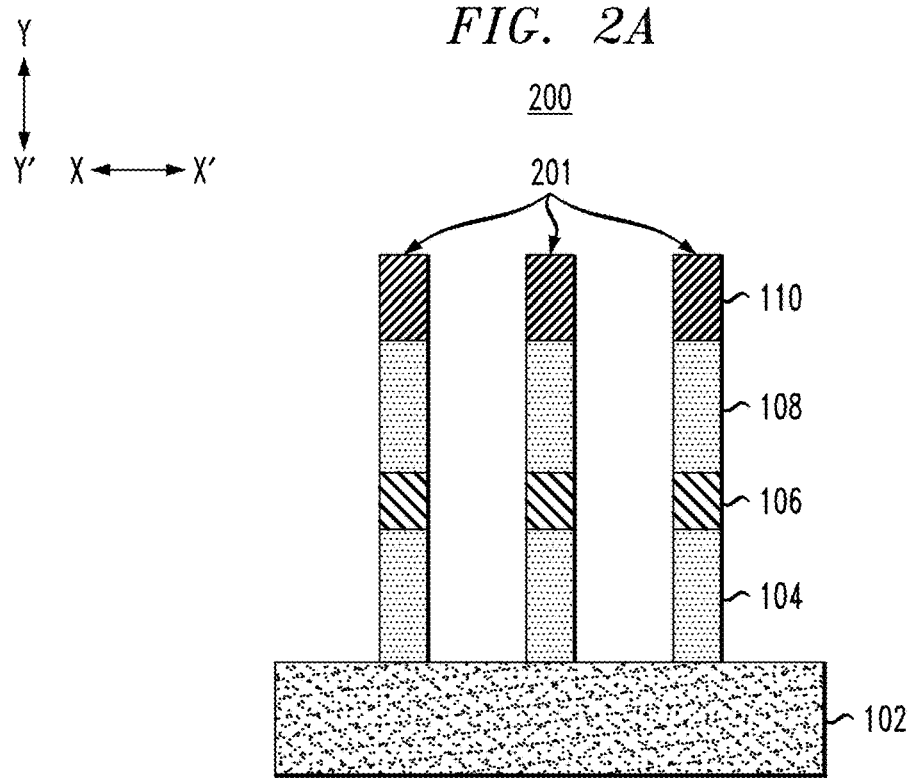
FIG. 2A depicts a side cross-sectional view of the FIG. 1 semiconductor structure following patterning of pillars, according to an embodiment of the invention.

Illustrative embodiments of the invention may be described herein in the context of illustrative methods for forming nanostructures including arrays of self-aligned nanotips, along with illustrative apparatus, systems and devices formed using such methods. However, it is to be understood that embodiments of the invention are not limited to the illustrative methods, apparatus, systems and devices but instead are more broadly applicable to other suitable methods, apparatus, systems and devices.

As mentioned above, nanotips may be used in various applications, including in applications that utilize an array of nanotips. It is challenging, however, to form large arrays of highly ordered nanotips with controllable shapes and dimensions. Embodiments provide techniques for forming high-density vertically self-aligned tip to tip arrays of nanotips. Advantageously, self-aligned nanotips formed as described herein can be fabricated in-situ with silicon integrated circuit manufacturing processes without additional equipment or chemistries.

Reducing dimensions of a material system down to nanoscale will modify electronic states because of quantum confinement, leading to different properties (e.g., optical, electrical, mechanical, etc.) compared with bulk material. Compared with bulk materials, one significant characteristic of nanostructure material is its high surface-to-volume ratio. In a gas ionization sensor application, conventional gas sensors based on gas ionization are often limited by bulky architecture, high power consumption and high voltage operation. Gas ionization sensors made or formed with nanostructures or nanotips as described herein offer various advantages, including low voltage operation, fast resetting, high sensitivity and high selectivity.

Embodiments provide techniques for forming nanostructures on a substrate. In some embodiments, the nanostructures comprise an array of vertically self-aligned pairs of nanotips on a substrate. The nanotips may have a vertical semiconductor material (e.g., germanium (Ge)) concentration gradient going from an apex or point to a base of the nanotips (e.g., of decreasing Ge concentration as distance from a point of the tip increases). The concentration gradient results in a band gap gradient in the nanotips.

As will be described in further detail below with respect to FIGS. 1-8, an array of self-aligned pairs of nanotips may be fabricated on a substrate by depositing a film stack (e.g., a silicon (Si) layer followed by a silicon germanium (SiGe) layer followed by another Si layer) on the substrate. The stack is patterned into pillars, with each pillar having a nitride hard mask on a top surface thereof. An oxide is filled to surround the pillars, and then recessed to expose at least a portion of the top of the film stack below the hard mask. A nitride is deposited on the sidewalls of the pillars, forming nitride rings around each pillar, with nitride rings around closest pillars pinching off and leaving gaps among the pillars. The nitride is etched to expose the oxide in the nitride gap areas. A thermal oxidation is then performed, which forms sharp tips in the pairs of nanotip pillars at or proximate to a vertical center of each pillar pair. The sharp tips are formed due to the graded concentration of Ge in the pillars. The higher Ge content central portion of the pillar film stack oxidizes faster than the vertical regions away from the center, resulting in tapered pairs of vertically self-aligned sharp nanotips embedded in the oxide. The nanotip array may then be subject to further processing, such as to form a sensor or other desired structure utilizing an array of nanostructures formed as described herein.

Illustrative processes for forming arrays of self-aligned nanotips on a surface of a semiconductor substrate will now be described with respect to FIGS. 1-8.

FIG. 1 depicts a side cross-sectional view 100 of a semiconductor structure, comprising a substrate 102 with a film stack comprising layers 104, 106 and 108 formed over a top surface thereof. In some embodiments, the substrate 102 comprises a semiconductor substrate, such as a bulk silicon substrate, although other suitable semiconductor materials may be used. The semiconductor material can include one or more monocrystalline silicon materials, such as the relatively pure or lightly impurity-doped monocrystalline silicon materials typically used in the semiconductor industry, as well as polycrystalline silicon materials, wherein silicon can be mixed with other elements such as carbon and the like. Illustrative examples of silicon-containing materials suitable for the bulk semiconductor substrate 102 include, but are not limited to, silicon (Si), silicon germanium (SiGe), silicon germanium carbide (SiGeC), silicon carbide (SiC), polysilicon (poly-Si), epitaxial silicon, amorphous silicon (a-Si), and multi-layers thereof. The semiconductor material used for substrate 102 may also or alternatively include other materials such as relatively pure and impurity-doped gallium arsenide (GaAs), germanium (Ge), gallium nitride (GaN), cadmium telluride (CaTe), zinc selenide (ZnSe), zinc oxide (ZnO), glass, and the like. The silicon substrate 102 can be a bulk silicon wafer or can be a thin layer of silicon disposed over an insulating layer (SOI) that, in turn, can be supported by a carrier wafer. The substrate 102 can be material consisting essentially of III-V compound semiconductors or II-VI compound semiconductors.

The substrate 102 may have a width or horizontal thickness (in direction X-X') that varies, such as based on the desired number of nanotip structures or pillars that are to be patterned. The substrate 102 may have a height or vertical thickness (in direction Y-Y') ranging from 10 micrometers (μm) to 1 millimeter (mm).

The film stack comprises a first layer 104, a second layer 106 and a third layer 108. The first layer 104 and the third layer 108 may each be formed of Si, while the second layer 106 is formed of SiGe. Other film stack options for layers 104/106/108 include: Si/Ge/Si, undoped semiconductor (e.g., Si)/doped semiconductor (e.g., doped Si)/undoped semiconductor (e.g., Si), etc. Dopants can be n-type (e.g., phosphorus (P), arsenic (As), etc.), p-type (e.g., boron (B), etc.), fluorine, etc. Dopants can be used to enhance oxidation rate of the second layer 106. More generally, the second layer 106 is formed of, or contains, a material that oxides faster than material of the first layer 104 and third layer 108 to form nanotip structures with sharp points as described in further detail below. For the purposes of description below, it is assumed that the second layer 106 is formed of SiGe, or as multiple layers of SiGe with varying concentration of Ge. The multiple layers of SiGe forming the second layer 106 may form a vertical concentration profile where there is a highest or higher percentage of Ge in a vertical center of the film stack, and where the concentration of Ge decreases as distance from the vertical center increases. Further details regarding the graded concentration will be described below with respect to FIGS. 5 and 6.

The first layer 104 and the third layer 108 may each have a height or vertical thickness (in direction Y-Y') ranging from 20 nanometers (nm) to 200 nm, although other thicknesses that are greater or less than this range may be employed as desired depending on the particular application. The second layer 106 may have a height or vertical thickness (in direction Y-Y') ranging from 5 nm to 50 nm, although other thicknesses that are greater or less than this range may be employed as desired depending on the particular application.

Figure 2B:
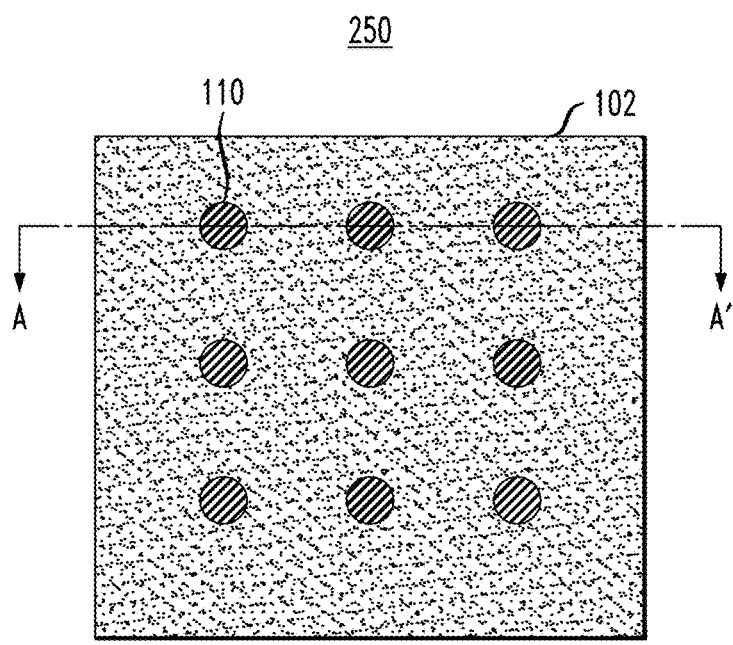
FIG. 2B depicts a top-down view of the FIG. 2A structure, according to an embodiment of the invention.

FIG. 2A depicts a side cross-sectional view 200 of the FIG. 1 structure following patterning of pillars 201 from the film stack. The side cross-sectional view 200 is taken along the line A-A' in the top-down view 250 of FIG. 2B. In the FIG. 2 example, a 3×3 array of pillars 201 is formed. It is to be appreciated, however, that different numbers of pillars may be formed as desired for a particular application. Further, while FIGS. 2A and 2B illustrate an example of cylindrical or rounded pillars, this is not a requirement. In other embodiments, the pillars may be square or rectangular, or another desired shape. In some embodiment, combinations of different shaped pillars may be formed on a substrate, such as forming one or more cylindrical pillars and one or more rectangular pillars on a same substrate. Also, while FIGS. 2A and 2B (and other figures herein) show each of the pillars 201 having a same size, this is not a requirement. In some embodiments, pillars of different sizes (e.g., different heights, different widths or radius, etc.) may be formed.

The pillars 201 may be patterned using various techniques, such as using sidewall image transfer (SIT) patterning techniques, lithography, etc. Each of the pillars 201 has a hard mask 110 formed over a top surface thereof. The hard mask 110 may be a nitride such as silicon nitride (SiN). Alternative hard mask materials include, by way of example, silicon oxide (SiO), a silicon oxynitride (SiON), a silicon carbonitride (SiCN), a silicon boronitride (SiBN), a silicon borocarbide (SiBC), a silicon boro carbonitride (SiBCN), a boron carbide (BC), a boron nitride (BN), or combinations thereof. The hard mask 110 has a height or vertical thickness (in direction Y-Y') ranging from 5 nm to 60 nm, although other thicknesses that are greater or less than this range may be employed as desired depending on the particular application.

Figure 3A:
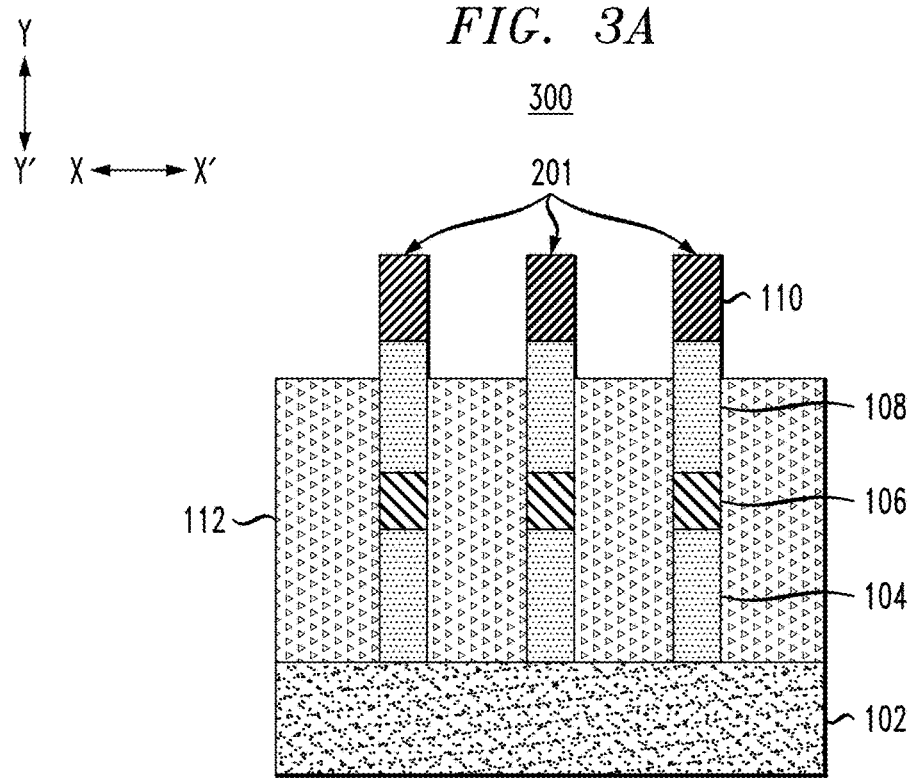
FIG. 3A depicts a side cross-sectional view of the structure shown in FIGS. 2A and 2B following fill and recess of an oxide, according to an embodiment of the invention.

FIG. 3A depicts a side cross-sectional view 300 of the structure shown in FIGS. 2A and 2B, following fill and recess of an oxide 112. The side cross-sectional view 300 is taken along the line A-A' in the top-down view 350 of FIG. 3B. The oxide 112 may be silicon oxide (SiO), low-temperature oxide (LTO), high-temperature oxide (HTO), flowable oxide (FOX) or some other dielectric, which can be selectively removed relative to material of the pillars 201 and hard mask 110. The oxide 112 may be filled to completely cover the pillars 201, followed by a recess below a bottom surface of the hard mask 110 exposing at least a portion of the sidewalls of the film stack of each pillar (e.g., a portion of the third layer 108). The oxide 112 may have a height or vertical thickness (in direction Y-Y'), measured from a top surface of the substrate 102, ranging from 80 nm to 150 nm, although other thicknesses that are greater or less than this range may be employed as desired depending on the particular application.

Figure 3B:
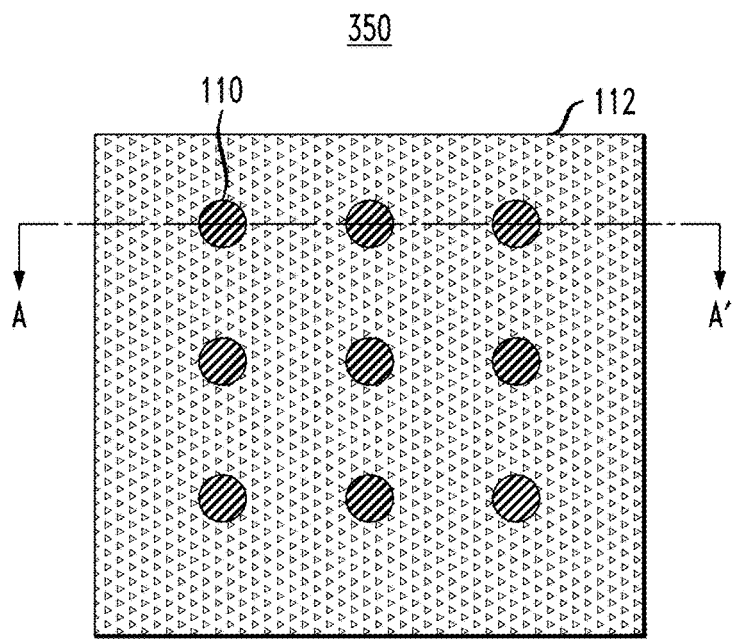
FIG. 3B depicts a top-down view of the FIG. 3A structure, according to an embodiment of the invention.
Figure 4A:
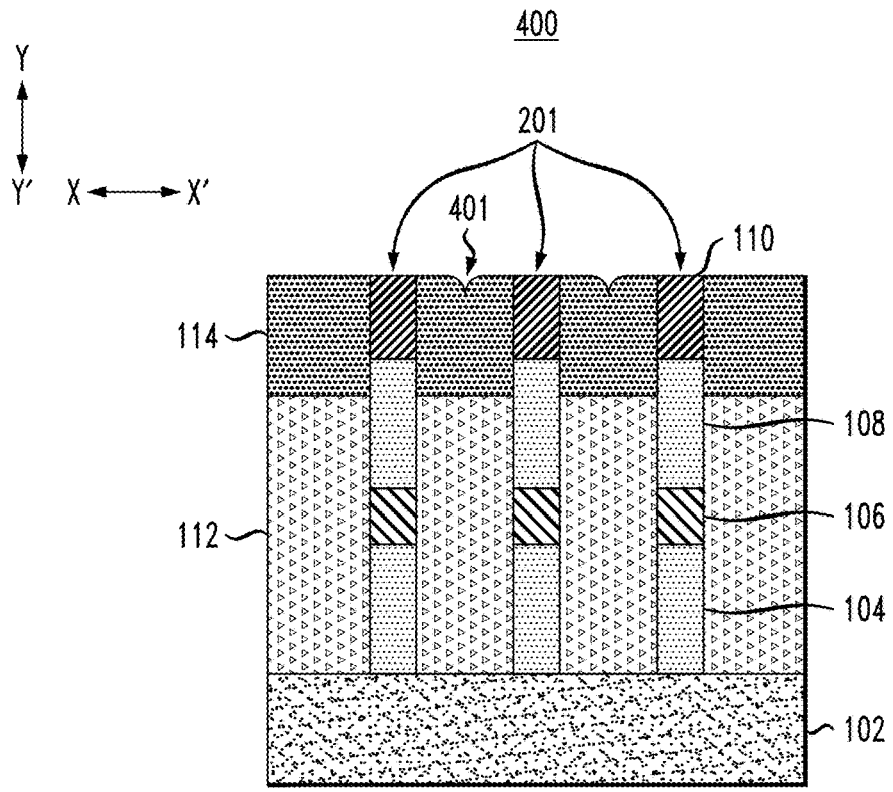
FIG. 4A depicts a side cross-sectional view of the structure shown in FIGS. 3A and 3B following formation of a nitride on exposed sidewalls of the pillars, according to an embodiment of the invention.
Figure 4B:
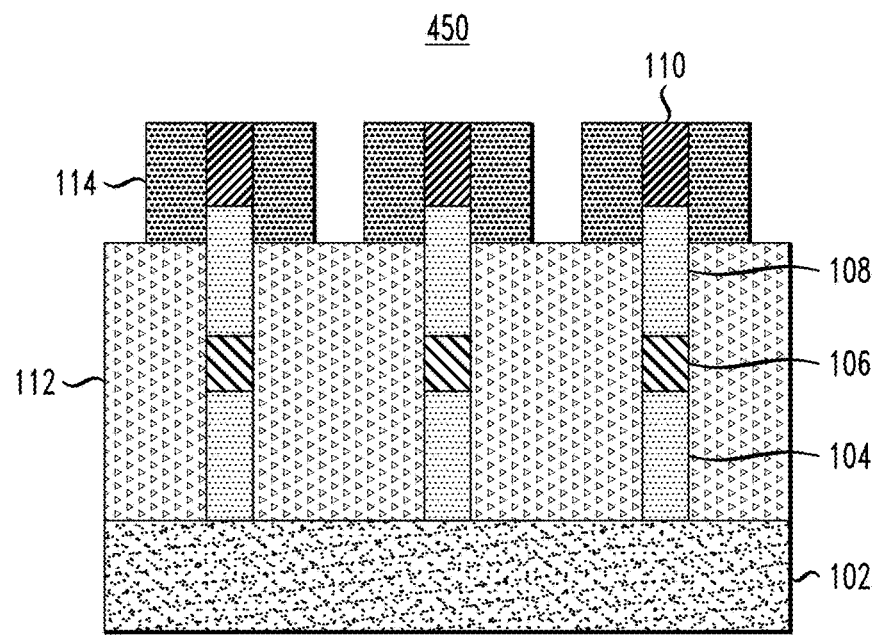
FIG. 4B depicts another side cross-sectional view of the structure shown in FIGS. 3A and 3B following formation of the nitride on the exposed sidewalls of the pillars, according to an embodiment of the invention.

FIG. 4A depicts a side cross-sectional view 400 of the structure shown in FIGS. 3A and 3B, following formation of a nitride 114 on exposed sidewalls of the pillars 201. FIG. 4B depicts another side cross-sectional view 450 of the structure shown in FIGS. 3A and 3B following formation of the nitride 114. The side cross-sectional view 400 is taken along the line A-A' in the top-down view 475 of FIG. 4C, and the side cross-sectional view 450 is taken along the line B-B' in the top-down view 475 of FIG. 4C.

Figure 4C:
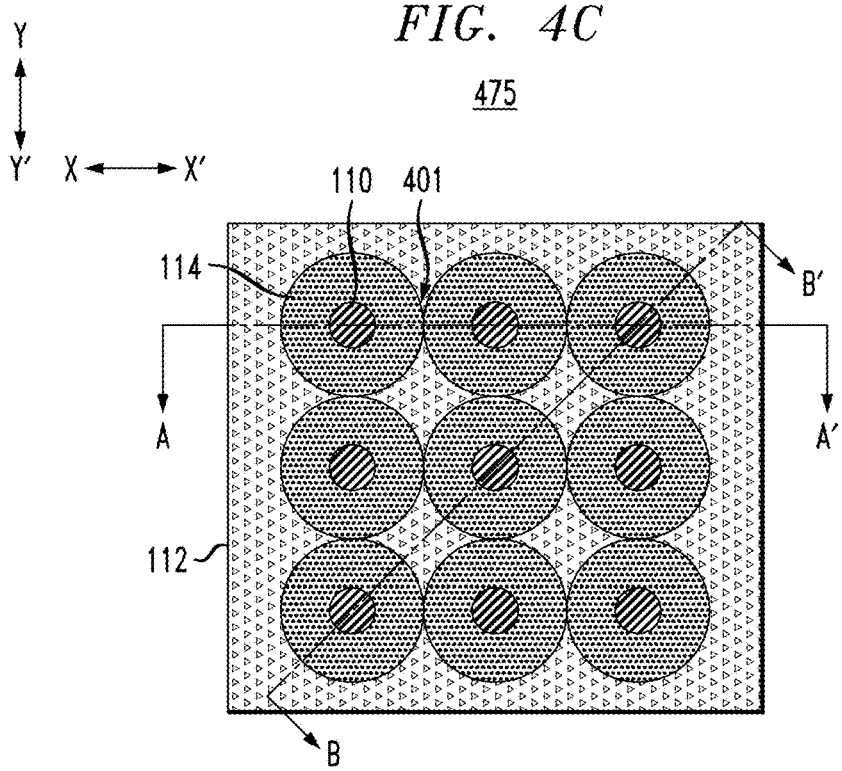
FIG. 4C depicts a top-down view of the structure shown in FIGS. 4A and 4B, according to an embodiment of the invention.

As illustrated in FIGS. 4A-4C, the nitride 114 is deposited on the sidewalls of the pillars 201 so as to form nitride rings around each of the pillars. Nitride rings around closest pillars pinch off as indicated by element 401, leaving gaps among the pillars. The nitride 114 may be etched, using directional reactive-ion etching (RIE) or another suitable etch process, to expose the oxide 112 in nitride gap areas. The nitride 114 may comprise an insulating material. Non-limiting examples of suitable insulating materials include SiO, a silicon nitride such as $Si_3N_4$, SiOCN, SiBCN, or any combination thereof.

The remaining nitride 114, also referred to herein as a top nitride plate, serves as an anchor plane to hold the pillars 201 in place during a subsequent thermal anneal and/or oxidation process described in further detail below. In some embodiments, the oxide 112 may be etched away before the thermal anneal and oxidation process. Oxide 112 can be removed by a wet etch process which is performed selectively with respect to the material of the nitride plate 114 and the material of pillars 201. For example, a wet etching solution containing hydrofluoric acid can be used to selectively remove oxide 112.

The thermal anneal and oxidation process will now be described in further detail with respect to FIGS. 5 and 6. The thermal anneal process may be performed in an inert environment, such as nitrogen or argon. During the anneal process, the germanium inside the SiGe layer 106 will diffuse from a higher germanium concentration region to a lower germanium concentration region (e.g., upward and downward to layer 108 and layer 104 respectively). In the context of the exemplary embodiments, the germanium will diffuse from the SiGe layer 106 along two directions so eventually a SiGe layer with graded germanium concentration is formed.

Figure 5:
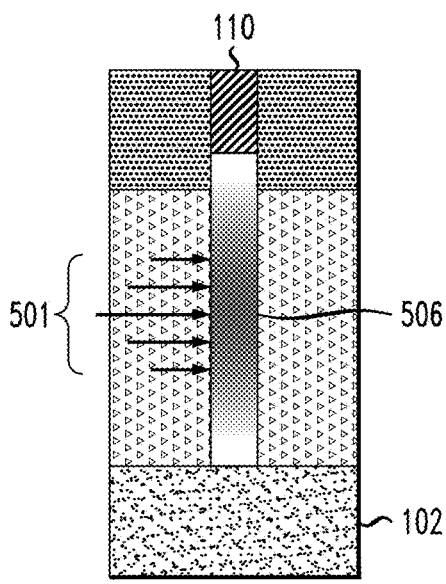
FIG. 5 depicts a side cross-sectional view of a portion of the structure shown in FIGS. 4A-4C showing a pillar comprising a profile with graded concentration of a semiconductor material, according to an embodiment of the invention.

FIG. 5 depicts a side cross-sectional view 500 of a portion of the structure shown in FIGS. 4A-4C. More particularly, the side cross-sectional view 500 shows one of the pillars 201 having a vertical profile with graded concentration of a semiconductor material, denoted as 506. The semiconductor material may be SiGe, and the graded concentration may be one such that the vertical center of the pillar 506 has a highest Ge concentration, with lower Ge concentration as distance from the vertical center increases. This is illustrated in FIG. 5 by the gradient shading of pillar 506, with dark shading corresponding to higher Ge concentration. The arrows 501 further indicate the graded concentration, where longer ones of the arrows correspond to higher Ge concentration.

In an alternative embodiment, layer 106 in FIG. 1 can be a directly deposited graded SiGe layer 106 on layer 104. Graded concentrations of germanium percentage may be achieved by recipe adaptation such as by varying the germanium precursor flow. Additionally, pressure may also be used to optimize uniformity of thickness of the multiple concentrations of germanium. The SiGe gradient layer 106 may thus be created by depositing a graded SiGe layer by chemical vapor deposition (CVD) or a similar process. Initially, the precursor gases would comprise all silicon precursor gas or at least a very low germanium precursor gas flow. Thereafter, the silicon precursor gas flow would be gradually decreased while the germanium precursor gas flow would be gradually increased until the desired half thickness of the SiGe gradient layer 106 has been achieved, then the silicon precursor gas flow would be gradually increased while the germanium precursor gas flow would be gradually decreased until the desired second half thickness of the SiGe gradient layer 106 has been achieved. It is also within the scope of the exemplary embodiments to deposit a SiGe gradient layer 106, as just described, and then perform the thermal annealing as described above, either in an inert atmosphere or in an oxidation environment, to modulate the germanium concentration to any desired gradient.

Figure 6:
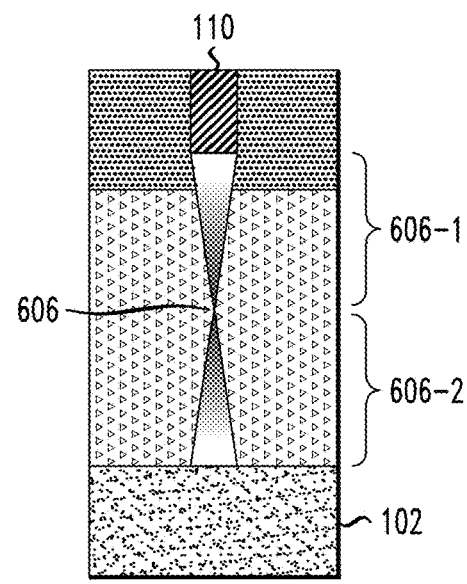
FIG. 6 depicts a side cross-sectional view of the FIG. 5 structure following oxidation, according to an embodiment of the invention.

FIG. 6 depicts a side cross-sectional view 600 of the FIG. 5 structure, following oxidation. The thermal oxidation may be performed in an oxidation process containing oxygen or water vapor. In some embodiments, the oxidation is a thermal oxidation at a temperature in the range of 700 degrees Celsius (° C.) to about 1250° C. The anneal process may be furnace anneal, rapid thermal anneal, flash anneal, or any suitable combination of these processes. The anneal time may range from about 1 millisecond (ms) to about 2 hours, depending on the anneal temperature. In another embodiment, the oxidation processing conditions may include an oxygen pressure of 10 Torr to 1000 Torr and a temperature of 700° C. to 1250° C. for 1 second to 30 minutes, depending on the temperature and oxygen pressure. Higher anneal temperatures may require shorter anneal times. A typical anneal condition may be about 10 minutes at 1000° C.

During the thermal oxidation, portions of the pillar 506 with a higher percentage or concentration of Ge have a higher oxidation rate. During oxidation, the oxygen is attracted to the silicon in the pillar 506 but not to the germanium. The silicon in the pillar 506 and oxygen react to form silicon oxide so that the silicon in the pillar 506 moves outwardly from the SiGe portion into the oxide 112. The germanium in the pillar 506, however, is repelled to the center core of the pillar 506. With respect to the portions of the pillar 506, the higher the germanium concentration, the faster the oxidation rate. Consequently, the center portion in the pillar 506, having a higher or highest germanium concentration, oxidizes faster than the upper and lower portion of pillar 506, having a lower germanium concentration. As a result, the oxidation results in formation of a nanotip pillar pair 606. The nanotip pillar pair 606 comprises a bottom nanotip denoted 606-1 and a top nanotip denoted 606-2. The bottom and top nanotips of nanotip pillar pair 606 have a highest concentration of Ge at the sharp tips thereof, with a graded vertical profile concentration of Ge that decreases down to respective base portions. The bottom nanotip 606-1 has a base portion disposed on the top surface of the substrate 102 with tapered sidewalls forming a sharp tip at or proximate to a vertical center of the nanotip pillar pair 606. The top nanotip 606-2 has a base portion disposed or anchored in the nitride 114 with tapered sidewalls forming a sharp tip at or proximate to the vertical center of the nanotip pillar pair 606.

Figure 7A:
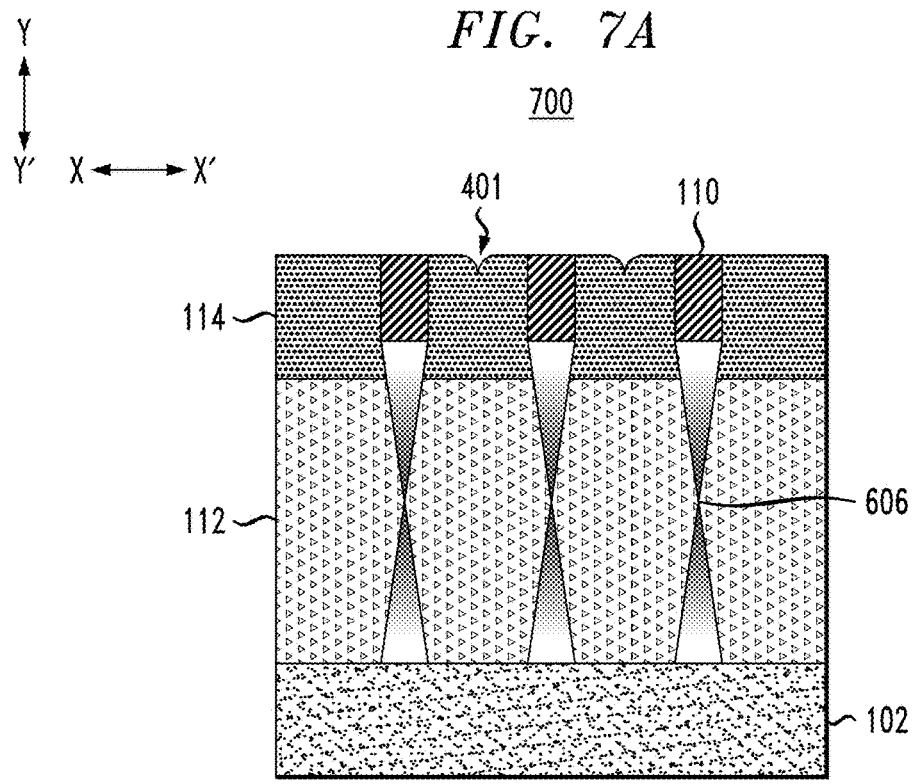
FIG. 7A depicts a side cross-sectional view of the structure shown in FIGS. 4A-4C following oxidation of the pillars, according to an embodiment of the invention.
Figure 7B:
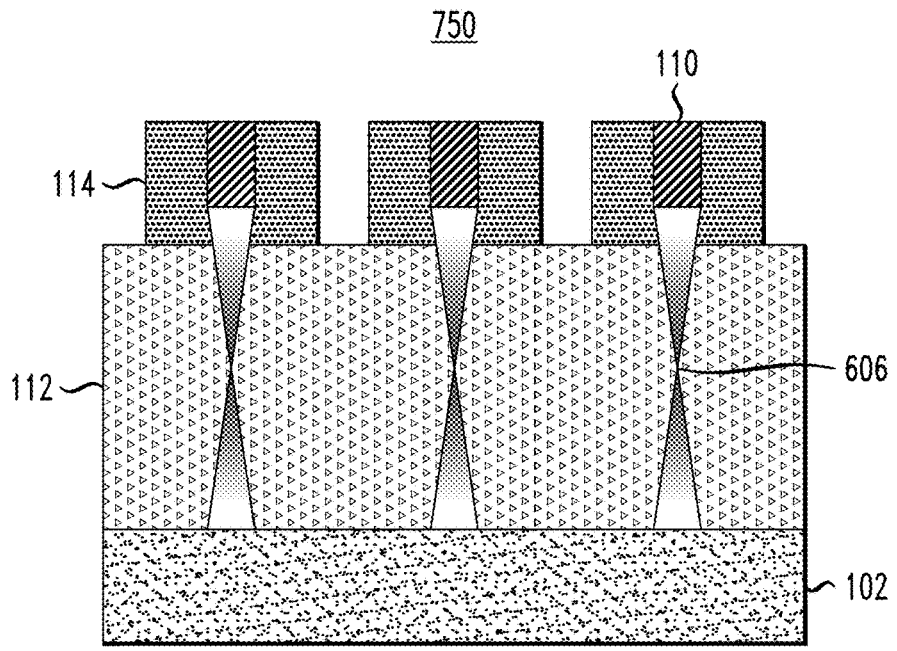
FIG. 7B depicts another side cross-sectional view of the structure shown in FIGS. 4A-4C following oxidation of the pillars, according to an embodiment of the invention.
Figure 7C:
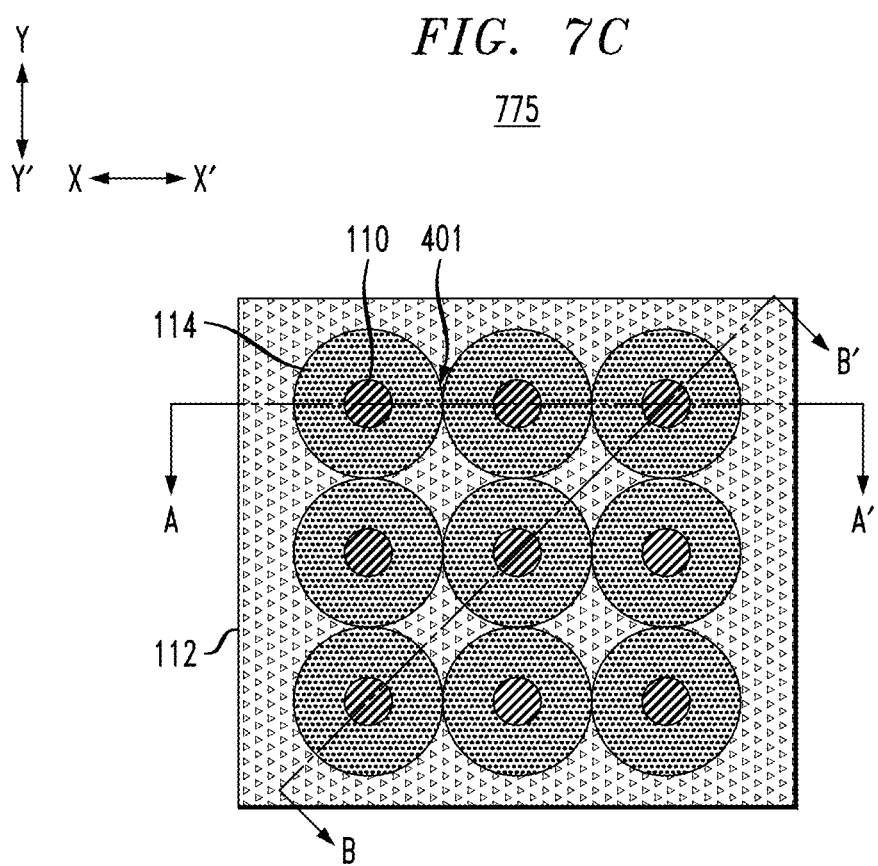
FIG. 7C depicts a top-down view of the structure shown in FIGS. 7A and 7B, according to an embodiment of the invention.

FIG. 7A depicts a side cross-sectional view 700 of the structure shown in FIGS. 4A-4C, following an oxidation process as described above with respect to FIGS. 5 and 6. FIG. 7B depicts another side cross-sectional view 750 of the structure shown in FIGS. 4A-4C following the oxidation process describe above with respect to FIGS. 5 and 6. The side cross-sectional view 700 is taken along the line A-A' in the top-down view 775 of FIG. 7C, and the side cross-sectional view 750 is taken along the line B-B' in the top-down view 775 of FIG. 7C. FIGS. 7A-7C illustrate vertically self-aligned nanotip arrays provided by nanotip pillar pairs 606. The sharp tip of the top and bottom nanotips in each nanotip pillar pair may have a radius dimension of about 2 nm to 5 nm. In another exemplary embodiment, the dimension may be about 5 nm to 50 nm. Nanotips with a radius dimension less than about 2 nm or greater than about 50 nm may also be formed. The nanotip pillar pairs 606 may be further doped to lower their resistance. For example, nanotip pillar pairs 606 may be doped with p-type or n-type dopants. N-type dopants may include P, As, antimony (Sb), etc. P-type dopants may include B, gallium (Ga), and indium (In). In some embodiments, the nanotip pillar pairs 606 are doped after nanotip formation. In other embodiments, the nanotip pillar pairs 606 may be doped earlier such as when the source layers of nanotip pillar pairs 606 are initially formed, or at another time before nanotip formation.

Figure 8A:
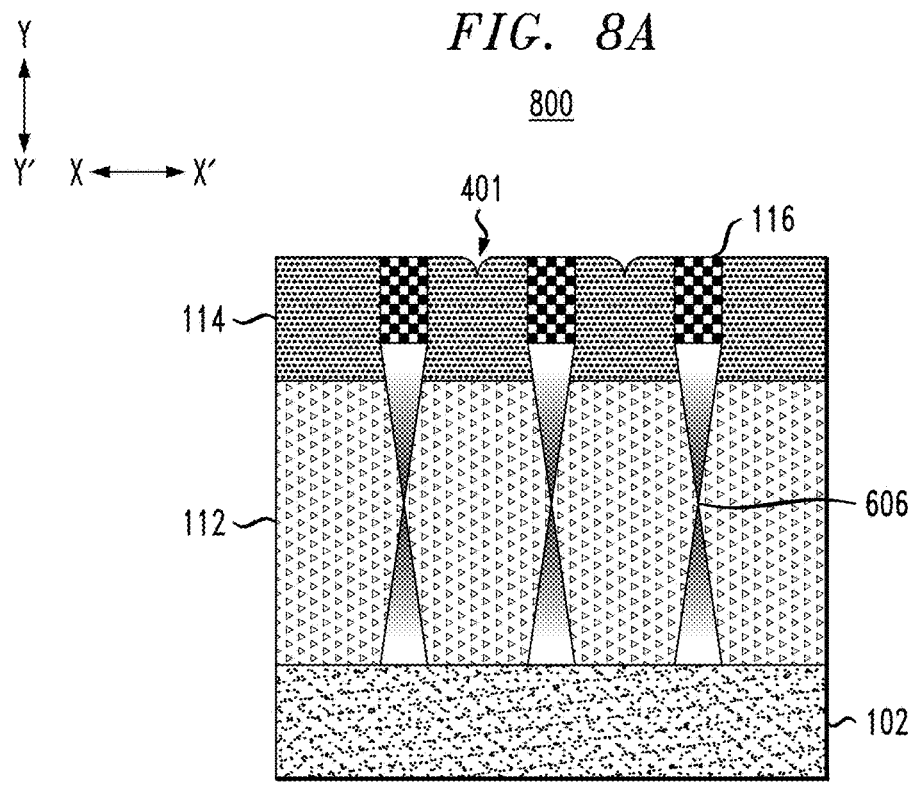
FIG. 8A depicts a side cross-sectional view of the structure shown in FIGS. 7A-7C following removal of the hard mask formed over the pillars and formation of epitaxial layers on a top surface of the pillars, according to an embodiment of the invention.
Figure 8B:
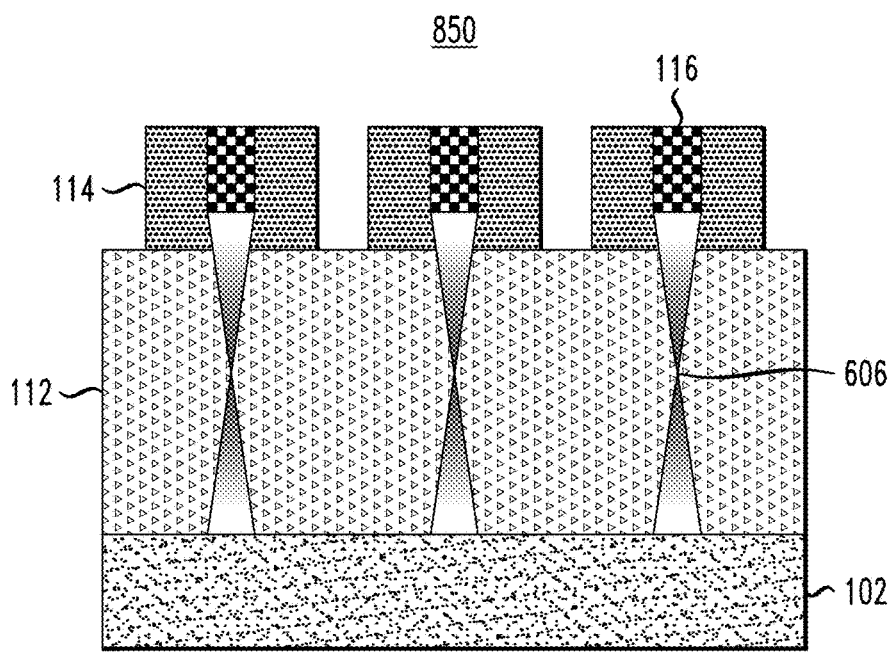
FIG. 8B depicts another side cross-sectional view of the structure shown in FIGS. 7A-7C following removal of the hard mask formed over the pillars and formation of the epitaxial layers on the top surface of the pillars, according to an embodiment of the invention.
Figure 8C:
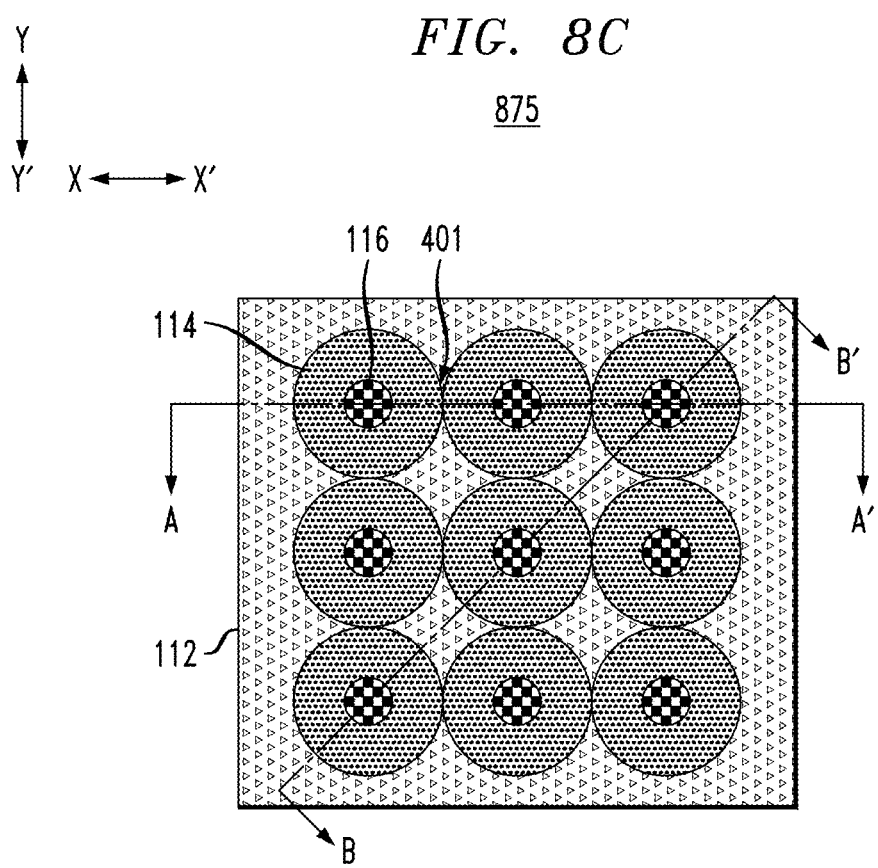
FIG. 8C depicts a top-down view of the structure shown in FIGS. 8A and 8B, according to an embodiment of the invention.

FIG. 8A depicts a side cross-sectional view 800 of the structure shown in FIGS. 7A-7C following removal of the hard mask 110 formed over the nanotip pillar pairs 606, and following formation of epitaxial layers 116 over top surfaces of the nanotip pillar pairs 606 exposed after removal of the hard mask 110. FIG. 8B depicts another side cross-sectional view 850 of the structure shown in FIGS. 8A-8C following removal of hard mask 110 and formation of epitaxial layers 116. The side cross-sectional view 800 is taken along the line A-A' in the top-down view 875 of FIG. 8C, and the side cross-sectional view 850 is taken along the line B-B' in the top-down view 875 of FIG. 8C. The structure shown in FIGS. 8A-8C may be subject to further processing for formation of metal contacts. Such processing may include deposition of an interlayer dielectric (ILD), contact trench patterning, and metal filling, etc.

Figure 9:
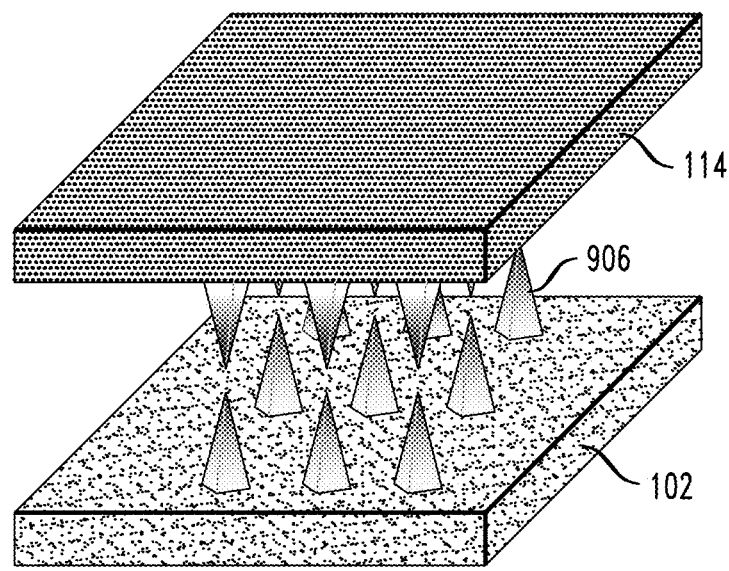
FIG. 9 depicts a perspective view of a structure with an array of pairs of self-aligned rectangular nanotip pillars, according to an embodiment of the invention.

FIG. 9 depicts a perspective view 900 of a structure with an array of self-aligned nanotip pillar pairs 906. More particularly, FIG. 9 illustrates a structure with rectangular nanotip pillar pairs 906. The nanotip pillar pairs 906 may be formed using processing similar to that described above with respect to FIGS. 1-8, although the initial pillar patterning forms rectangular pillars rather than cylindrical or rounded pillars. The bottoms of the nanotip pillar pairs 906 are formed over substrate 102, and the tops of the nanotip pillar pairs 906 are anchored in the nitride 114. The oxide 112 is not shown in the perspective view 900. As described above, the oxide 112 may be removed prior to the thermal oxidation. The nanotip pillar pairs 906 have a highest concentration of Ge at the sharp tips thereof, with a graded vertical profile concentration of Ge that decreases down to the base (for the bottoms of the nanotip pillar pairs 906 the base is the substrate 102, and for the tops of the nanotip pillar pairs 906 the base is anchored in the nitride 114).

Figure 10:
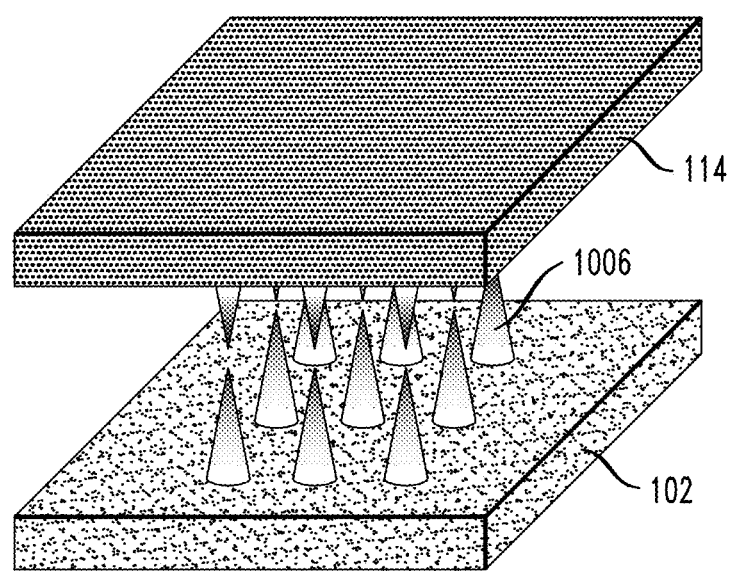
FIG. 10 depicts a perspective view of a structure with an array of self-aligned cylindrical nanotip pillars, according to an embodiment of the invention.

FIG. 10 depicts a perspective view 1000 of a structure with an array of self-aligned nanotip pillar pairs 1006. More particularly, FIG. 1 illustrates a structure with cylindrical or rounded nanotip pillar pairs 1006 formed using processing similar to that described above with respect to FIGS. 1-8. The bottoms of the nanotip pillar pairs 1006 are formed over substrate 102, and the tops of the nanotip pillar pairs 1006 are anchored in the nitride 114. The oxide 112 is not shown in the perspective view 1000. As described above, the oxide 112 may be removed prior to the thermal oxidation. The nanotip pillar pairs 1006 have a highest concentration of Ge at the sharp tips thereof, with a graded vertical profile concentration of Ge that decreases down to the base (for the bottoms of the nanotip pillar pairs 1006 the base is the substrate 102, and for the tops of the nanotip pillar pairs 1006 the base is anchored in the nitride 114).

Illustrative embodiments advantageously provide techniques for mass production of arrays of nanostructures using semiconductor processes. Such techniques permit formation of self-aligned vertical nanotip pair arrays, with good alignment from tip to tip. Each tip may have low and high band gap material with a gradient concentration as described above.

FIG. 11 depicts a perspective view 1100 of a sensor with an array of self-aligned cylindrical nanotip pillar pairs 1106. The sensor includes a substrate 1102 on which bottoms of the nanotip pillar pairs 1106 are disposed, with tops of the nanotip pillar pairs 1106 being anchored in nitride 1114. The substrate 1102, nanotip pillar pairs 1106 and nitride 1114 may be formed of similar materials and with similar sizing as the substrate 102, nanotip pillar pairs 606 and nitride 114 described above. Oxide spacers 1118 are formed surrounding portions of the array of nanotip pillar pairs 1106. A contact 1120 to the nanotip pillar pairs 1106 is formed over the nitride 1114. Although not shown in the perspective view 1100, epitaxial layers may be formed over the tops of the nanotip pillar pairs 1106 as described above, along with an ILD, etc. used in formation of contact 1120. The contact 1120 may be a metal contact, such as tungsten (W), nickel (Ni), titanium (Ti), molybdenum (Mo), tantalum (Ta), copper (Cu), platinum (Pt), silver (Ag), gold (Au), ruthenium (Ru), iridium (Ir), rhenium (Re), rhodium (Rh), and alloys thereof, polysilicon, or a conducting metallic compound material such as tantalum nitride (TaN), titanium nitride (TiN), tungsten silicide ($WSi_2$), tungsten nitride (WN), ruthenium oxide ($RuO_2$), cobalt silicide (CoSi), nickel silicide (NiSi), etc. The conductive material may further include dopants that are incorporated during or after deposition. When voltage is applied and a gas sample is introduced in the region surrounding the nanotip pillar pairs 1106, the voltmeter 1122 can sense the voltage and use the sensed voltage to determine features or parameters of the gas sample (e.g., identification of the gas type, concentration, etc.).

Figure 12A:
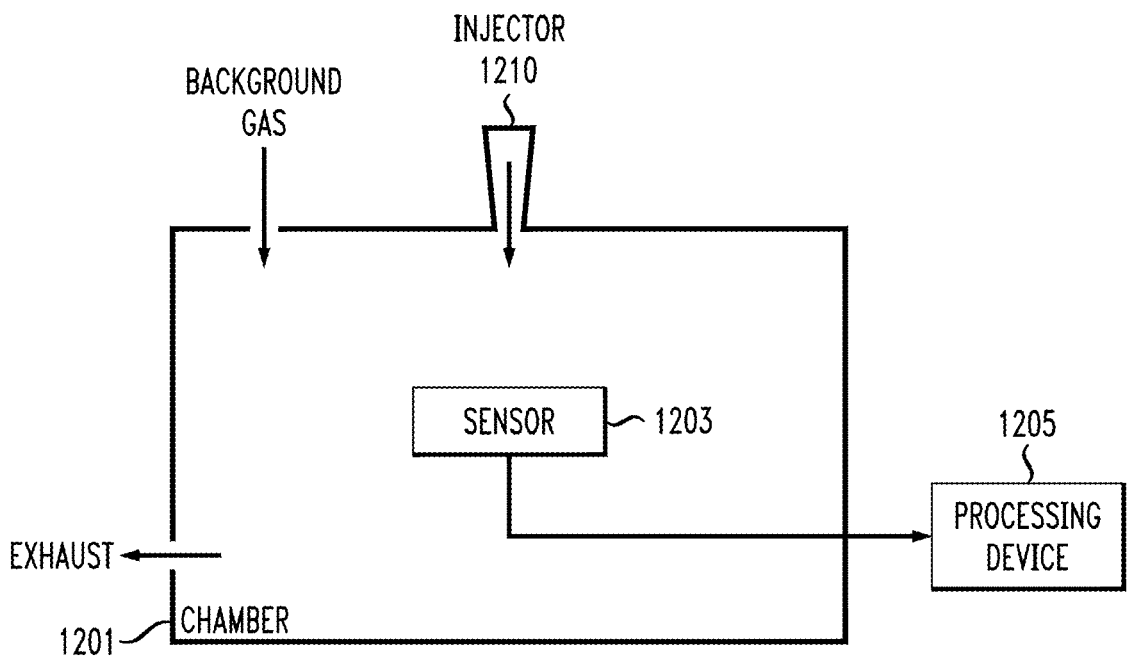
FIG. 12A depicts a gas ionization sensing system, according to an embodiment of the invention.

FIG. 12A depicts a gas ionization sensing system 1200. The gas ionization sensing system 1200 includes a chamber 1201, a sensor 1203 and a processing device 1205. The chamber 1201 includes an inlet where dry air (or another background gas) is introduced prior to measurement. After measurement of a gas sample, the background gas and gas sample are expelled from chamber 1201 via the outlet. The gas sample is introduced to chamber 1201 via an injector 1210 as shown. The processing device 1205, which may be a computing device such as a desktop, laptop, tablet, smartphone, etc. is configured to receive signals or measurements from the sensor 1203.

Figure 12B:
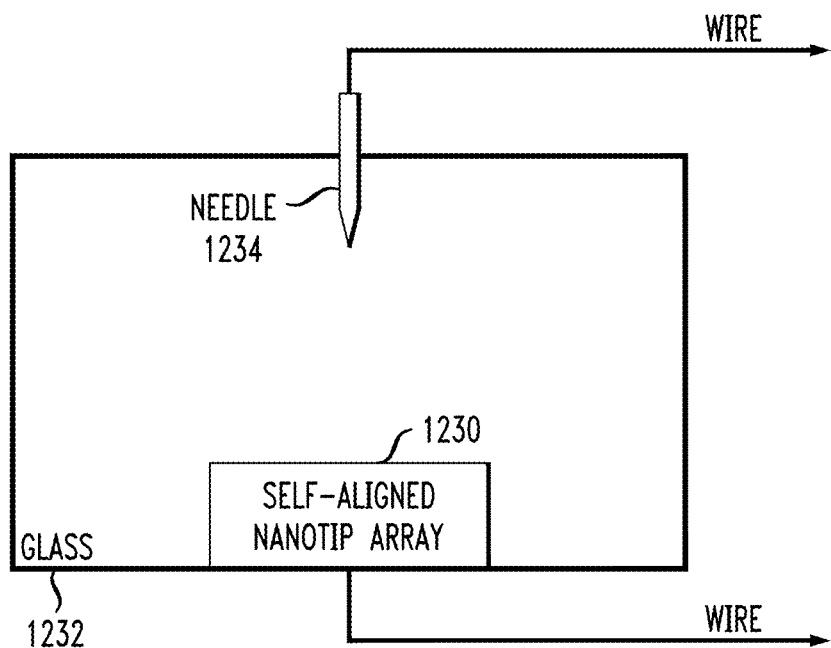
FIG. 12B depicts a detailed view of the sensor of the gas ionization sensing system of FIG. 12A utilizing a self-aligned nanotip array, according to an embodiment of the invention.

FIG. 12B depicts a detailed view of the sensor 1203 of the gas ionization sensing system 1200. The sensor 1203 includes a self-aligned nanotip array 1230 formed as described herein in a glass chamber 1232. Needle 1234 and the self-aligned nanotip array 1230 are connected via wires to a voltage source or voltmeter (not shown in FIG. 12B). The needle 1234 acts as a cathode, with the self-aligned nanotip array 1230 acting as the anode. Current or voltage measurements between the needle 1234 and self-aligned nanotip array 1230 are used for determining properties of a gas sample.

In some embodiments, a method of forming a semiconductor structure comprises forming a substrate, forming an anchor layer, and forming one or more self-aligned nanotip pillar pairs disposed vertically between the substrate and the anchor layer. A given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer. The bottom nanotip pillar and the top nanotip pillar comprise sidewalls that taper to points as distance from the respective base portions increases.

The given nanotip pillar pair may comprise a graded concentration of a semiconductor material which decreases in concentration as distance from a vertical center of the given nanotip pillar pair increases. The semiconductor material may comprise Ge.

In some embodiments, forming the one or more self-aligned nanotip pillar pairs comprises forming a film stack disposed over the top surface of the substrate, the film stack comprising the graded concentration of the semiconductor material, patterning a hard mask disposed over a top surface of the film stack, and performing SIT to form one or more pillars from the film stack. The method may further comprise filling an oxide disposed over the top surface of the substrate and over the one or more pillars and recessing the oxide to expose sidewalls of at least a portion of the film stack of the one or more pillars.

Forming the anchor layer may comprise depositing a nitride on the exposed sidewalls of the one or more pillars to form nitride rings around each of the one or more pillars, wherein the nitride rings around closest ones of the pillars pinch off leaving gap areas among the one or more pillars. The method may further comprise etching the nitride to expose a top surface of the oxide in the gap areas and performing a thermal oxidation. A rate of oxidization of the nanotip pillar pairs may be proportional to a concentration of the semiconductor material. Portions of the nanotip pillars with relatively higher concentration of the semiconductor material may oxidize faster than portions of the nanotip pillars with relatively lower concentration of the semiconductor material. The thermal oxidation may form the tapered sidewalls of the bottom nanotip pillar and the top nanotip pillar. The sidewalls of the bottom nanotip pillar and the top nanotip pillar may taper to respective points proximate the vertical center of the given nanotip pillar. In some embodiments, the oxide is removed prior to performing the thermal oxidation.

In some embodiments, the method further comprises removing the hard mask to expose top surfaces of the one or more nanotip pillars and forming epitaxial layers over the exposed top surfaces of the one or more nanotip pillars. The method may further comprise forming at least one contact to the epitaxial layers.

In some embodiments, a semiconductor structure comprises a substrate, an anchor layer, and one or more self-aligned nanotip pillar pairs disposed vertically between the substrate and the anchor layer. A given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer. The bottom nanotip pillar and the top nanotip pillar comprise sidewalls that taper to points as distance from the respective base portions increases. The given nanotip pillar pair may comprise a graded concentration of a semiconductor material which decreases in concentration as distance from a vertical center of the given nanotip pillar pair increases, and the semiconductor material may comprise Ge. The base portions of the bottom nanotip pillar and the top nanotip pillar maybe cylindrical, square, rectangular, etc.

In some embodiments, an integrated circuit comprises a gas ionization sensor comprising a substrate, an anchor layer, and one or more self-aligned nanotip pillar pairs disposed vertically between the substrate and the anchor layer. A given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer. The bottom nanotip pillar and the top nanotip pillar comprise sidewalls that taper to points as distance from the respective base portions increases.

It is to be appreciated that the various materials, processing methods (e.g., etch types, deposition types, etc.) and dimensions provided in the discussion above are presented by way of example only. Various other suitable materials, processing methods, and dimensions may be used as desired.

Semiconductor devices and methods for forming same in accordance with the above-described techniques can be employed in various applications, hardware, and/or electronic systems. Suitable hardware and systems for implementing embodiments of the invention may include, but are not limited to, sensors an sensing devices, personal computers, communication networks, electronic commerce systems, portable communications devices (e.g., cell and smart phones), solid-state media storage devices, functional circuitry, etc. Systems and hardware incorporating the semiconductor devices are contemplated embodiments of the invention. Given the teachings provided herein, one of ordinary skill in the art will be able to contemplate other implementations and applications of embodiments of the invention.

Various structures described above may be implemented in integrated circuits. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of forming a semiconductor structure, comprising:
    forming a substrate;
    forming an anchor layer; and
    forming one or more self-aligned nanotip pillar pairs disposed vertically between the substrate and the anchor layer;
    wherein a given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer;
    wherein the bottom nanotip pillar and the top nanotip pillar comprise sidewalls that taper to points as distance from the respective base portions increases; and
    wherein the given nanotip pillar pair comprises a graded concentration of a semiconductor material which decreases in concentration as distance from a vertical center of the given nanotip pillar pair increases.

2. The method of claim 1, wherein the semiconductor material comprises germanium (Ge).

3. The method of claim 1, wherein forming the one or more self-aligned nanotip pillar pairs comprises:
    forming a film stack disposed over the top surface of the substrate, the film stack comprising the graded concentration of the semiconductor material;
    patterning a hard mask disposed over a top surface of the film stack; and
    performing sidewall image transfer to form one or more pillars from the film stack.

4. The method of claim 3, further comprising:
    filling an oxide disposed over the top surface of the substrate and over the one or more pillars; and
    recessing the oxide to expose sidewalls of at least a portion of the film stack of the one or more pillars.

5. The method of claim 4, wherein forming the anchor layer comprises depositing a nitride on the exposed sidewalls of the one or more pillars to form nitride rings around each of the one or more pillars, wherein the nitride rings around closest ones of the pillars pinch off leaving gap areas among the one or more pillars.

6. The method of claim 5, further comprising etching the nitride to expose a top surface of the oxide in the gap areas.

7. The method of claim 6, further comprising performing a thermal oxidation.

8. The method of claim 7, wherein a rate of oxidization of the nanotip pillar pairs is proportional to a concentration of the semiconductor material.

9. The method of claim 7, wherein portions of the nanotip pillars with relatively higher concentration of the semiconductor material oxidize faster than portions of the nanotip pillars with relatively lower concentration of the semiconductor material.

10. The method of claim 7, wherein the thermal oxidation forms the tapered sidewalls of the bottom nanotip pillar and the top nanotip pillar.

11. The method of claim 10, wherein the sidewalls of the bottom nanotip pillar and the top nanotip pillar taper to respective points proximate the vertical center of the given nanotip pillar.

12. The method of claim 7, further comprising removing the oxide prior to performing the thermal oxidation.

13. The method of claim 7, further comprising:
    removing the hard mask to expose top surfaces of the one or more nanotip pillars; and
    forming epitaxial layers over the exposed top surfaces of the one or more nanotip pillars.

14. The method of claim 13, further comprising forming at least one contact to the epitaxial layers.

15. A semiconductor structure, comprising:
    a substrate;
    an anchor layer; and
    one or more self-aligned nanotip pillar pairs disposed vertically between the substrate and the anchor layer;
    wherein a given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer;

wherein the bottom nanotip pillar and the top nanotip pillar comprise sidewalls that taper to points as distance from the respective base portions increases; and wherein the given nanotip pillar pair comprises a graded concentration of a semiconductor material which decreases in concentration as distance from a vertical center of the given nanotip pillar pair increases.

16. The semiconductor structure of claim 15, wherein the semiconductor material comprises germanium (Ge).

17. The semiconductor structure of claim 15, wherein the base portions of the bottom nanotip pillar and the top nanotip pillar are cylindrical.

18. The semiconductor structure of claim 15, wherein the base portions of the bottom nanotip pillar and the top nanotip pillar are rectangular or square.

19. An integrated circuit comprising:
   a gas ionization sensor comprising:
      a substrate;
      an anchor layer; and
      one or more self-aligned nanotip pillar pairs disposed vertically between the substrate and the anchor layer;
   wherein a given one of the nanotip pillar pairs comprises a bottom nanotip pillar and a top nanotip pillar, the bottom nanotip pillar comprising a base portion disposed on a top surface of the substrate and the top nanotip pillar comprising a base portion disposed in the anchor layer;
   wherein the bottom nanotip pillar and the top nanotip pillar comprise sidewalls that taper to points as distance from the respective base portions increases; and
   wherein the given nanotip pillar pair comprises a graded concentration of a semiconductor material which decreases in concentration as distance from a vertical center of the given nanotip pillar pair increases.

20. The integrated circuit of claim 19, wherein the semiconductor material comprises germanium (Ge).

* * * * *